United States Patent [19]

Oftedal et al.

[11] Patent Number: 5,255,674
[45] Date of Patent: Oct. 26, 1993

[54] PORTABLE HEATING AND HUMIDIFYING DEVICE

[75] Inventors: Tor A. Oftedal, Oslo; Odd Halsnes, Maastad, both of Norway

[73] Assignee: Forsvarets Forskningsinstitutt, Kjeller, Norway

[21] Appl. No.: 766,735

[22] Filed: Sep. 27, 1991

[30] Foreign Application Priority Data

Sep. 28, 1990 [NO] Norway ............................ 904226

[51] Int. Cl.$^5$ .................. A61M 16/10; A62B 7/00
[52] U.S. Cl. ........................ 128/203.16; 128/203.26; 128/204.17; 128/203.29; 128/204.13; 128/203.17; 128/203.27
[58] Field of Search ................ 128/203.16, 203.17, 128/203.26, 203.27, 204.13, 204.14, 204.17, 203.29

[56] References Cited

U.S. PATENT DOCUMENTS

| | | | |
|---|---|---|---|
| 453,626 | 6/1891 | Coulter | 128/203.16 |
| 571,811 | 11/1896 | Valentine | 128/203.16 X |
| 1,485,260 | 2/1924 | Ernst | 128/203.27 |
| 3,115,134 | 12/1963 | Schmahl | 128/204.13 X |
| 3,565,071 | 2/1971 | Cobb et al. | 128/204.13 X |
| 3,637,978 | 1/1972 | Corbett et al. | 128/203.17 X |
| 3,695,267 | 10/1972 | Hirtz et al. | 128/203.17 |
| 3,983,869 | 10/1976 | Suzuki | 128/204.13 |
| 4,016,878 | 4/1977 | Castel et al. | |
| 4,026,285 | 5/1977 | Jackson | 128/204.13 X |
| 4,038,980 | 8/1977 | Fodor | 128/203.27 |
| 4,110,419 | 8/1978 | Miller | 128/204.13 X |
| 4,168,706 | 9/1979 | Fletcher et al. | 128/204.17 X |
| 4,288,396 | 9/1981 | Ottestad | 128/204.13 X |
| 4,664,674 | 5/1987 | Oftedal et al. | |
| 4,705,033 | 11/1987 | Halfpenney | 128/204.13 X |
| 4,825,863 | 5/1989 | Dittmar et al. | 128/203.27 |
| 5,038,769 | 8/1991 | Krauser | 128/203.27 |
| 5,148,801 | 9/1992 | Douwens et al. | 128/204.13 X |

FOREIGN PATENT DOCUMENTS

| | | |
|---|---|---|
| 1933350 | 1/1971 | Fed. Rep. of Germany. |
| 2020435 | 11/1971 | Fed. Rep. of Germany. |
| 2160561 | 6/1973 | Fed. Rep. of Germany. |
| 78035 | 4/1962 | France ......................... 128/204.17 |
| 1357022 | 2/1964 | France ......................... 128/203.27 |
| 127435 | 6/1973 | Norway. |
| 129772 | 5/1974 | Norway. |
| 133561 | 4/1960 | U.S.S.R. ..................... 128/204.17 |
| 197946 | 4/1924 | United Kingdom ......... 128/204.17 |

OTHER PUBLICATIONS

Alcatel Innova A/S, "Humipac" 1 page brochure (undated).
M. L. Collins, et al., "Accidental Hypothermia: An Experimental . . . ", Aviation, Space, and Environmental Medicine, Jul. 1977, pp. 625–632.
E. L. Lloyd, "Hypothermia and Cold Stress", Airway Warming, London, 1986, pp. 199–227.
J. S. Hayward, et al., "Accidental Hypothermia: An Experimental . . . ", Aviation, Space, and Environmental Medicine, Oct. 1985, pp. 1236–1240.

Primary Examiner—V. Millin
Assistant Examiner—Sebastiano Passaniti
Attorney, Agent, or Firm—Robbins, Berliner & Carson

[57] ABSTRACT

This invention relates to a portable heating and humidifying device which is effective in giving emergency therapy for accidental hypothermia. The device includes a charcoal fuel element heater (2;31) which is integrated with a moisturized element (1;32), so that heated air from the heater (2;31) is humidified by being passed through the moisturized element (1;32). The moisturized element contains a body (11;38) of water absorbent material, such as fibre wadding or foamed polymer. The body (11;38) of water absorbent material is contained within a heat conducting first housing (10;41), so as to leave a first airspace (13;41) between substantial parts of the outer surface of the body (11;38) and the inner surface of the first housing (10;41). The first housing (10;42) is arranged within a heat insulating second housing (15;50) defining a second airspace (16;45) through which dry warm air is transported to the face of person breathing the humidified air.

23 Claims, 4 Drawing Sheets

PORTABLE HEATING AND HUMIDIFYING DEVICE

TECHNICAL FIELD

The present invention relates to a heating and humidifying device for breathing apparatus, the heating. Such apparatus are known from e.g. U.S. Pat. No. 4,016,878 (Foundation for Ocean Research). This patent describes use of hydrogen catalytic combustion for the provision of heat and humidity to breathing air. This is, however, not suitable for field use because of the practical difficulties in regulating heat relative to the ambient temperature. The temperature of the breathing air is thus not as well controlled as required. The alternative use of oxygen instead of air which is normal in rescue operations, would create explosion danger. The construction shown is not suitable for use under cold conditions due to the cooling of the breathing air in the zone between the heating unit and the mouthpiece.

From Norwegian Patents Nos 127435 and 129772 (Hans Hirtz and Hanns-Joachim Hirtz, based on DE Applications Nos. P 19 33 350 / P 20 20 435 and P 21 60 561 respectively). There is known a device for treatment of the air ways with warm air. The use of an electric heating element requires an abundant electrical power source. This is very often not the case in the field. The described unit is not considered suitable in cold conditions because of the cooling of the breathing air in the mask and in the unit attached to the mask.

The present invention relates in particular to a portable heating and humidifying device which is effective in giving emergency therapy for accidental hypothermia. It has been accepted that inhalation of warm humidified air or airway rewarming improves the prognosis for persons who have been subjected to cold field and water environments.

This subject has been dealt with in detail in the following articles: 'Accidental Hypothermia: An Experimental Study of Practical Rewarming Methods' by M L Collins, A M Steinman and R D Chaney in Aviation, Space and Environmental Medicine, July, 1977 and by H S Hayward and A M Steinman in the same periodical of October, 1975. The subject of 'Airway Warming' has been treated in a book by Evan L Lloyd: 'Hypothermia and Cold Stress', Croon Helm, London (1986).

Persons climbing mountains and staying at high altitudes must inhale large volumes of environmental air in order to get enough oxygen. The inhaled air will take up moisture from the airways and lungs and be saturated with water vapor at a temperature close to the body temperature; The vaporization which requires heat therefore leads to a considerable loss of heat which will be greater the higher the altitude. High physical activity will increase the heat loss further, because the rate of respiration will increase correspondingly. The respiratoric heat losses of an injured person at high altitude can be fatal.

DISCLOSURE OF INVENTION

The object of the invention is to provide new and improved means for heating and-humidifying breathing air. Previously known airway warming apparatus are either not very effective, or they are too bulky and heavy to be practical for field use.

The invention thus provides a portable heating and humidifying device which is effective in giving emergency therapy for accidental hypothermia. The device preferably includes a charcoal fuel element heater which is integrated with a moisturized element, so that heated air from the heater is humidified by being passed through the moisturized element. The moisturized element contains a body of water absorbent material, such as fibre wadding or foamed polymer, which is contained within a heat conducting housing, so as to leave an airspace between substantial parts of the outer surface of the body and the inner surface of the housing. The housing is preferably arranged within a heat insulating second housing defining a second airspace through which dry warm air is transported to the face of the person breathing the humidified air. Practical use of the invention has shown that respiratoric heat losses of injured persons can be removed when the breathing air/oxygen is heated and humidified up to 100% relative humidity.

BRIEF DESCRIPTION OF DRAWING

Above mentioned and other features and objects of the present invention will clearly appear from the following detailed description of embodiments of the invention taken in conjunction with the drawings, where.

BEST MODE FOR CARRYING OUT THE INVENTION

Figure 1:
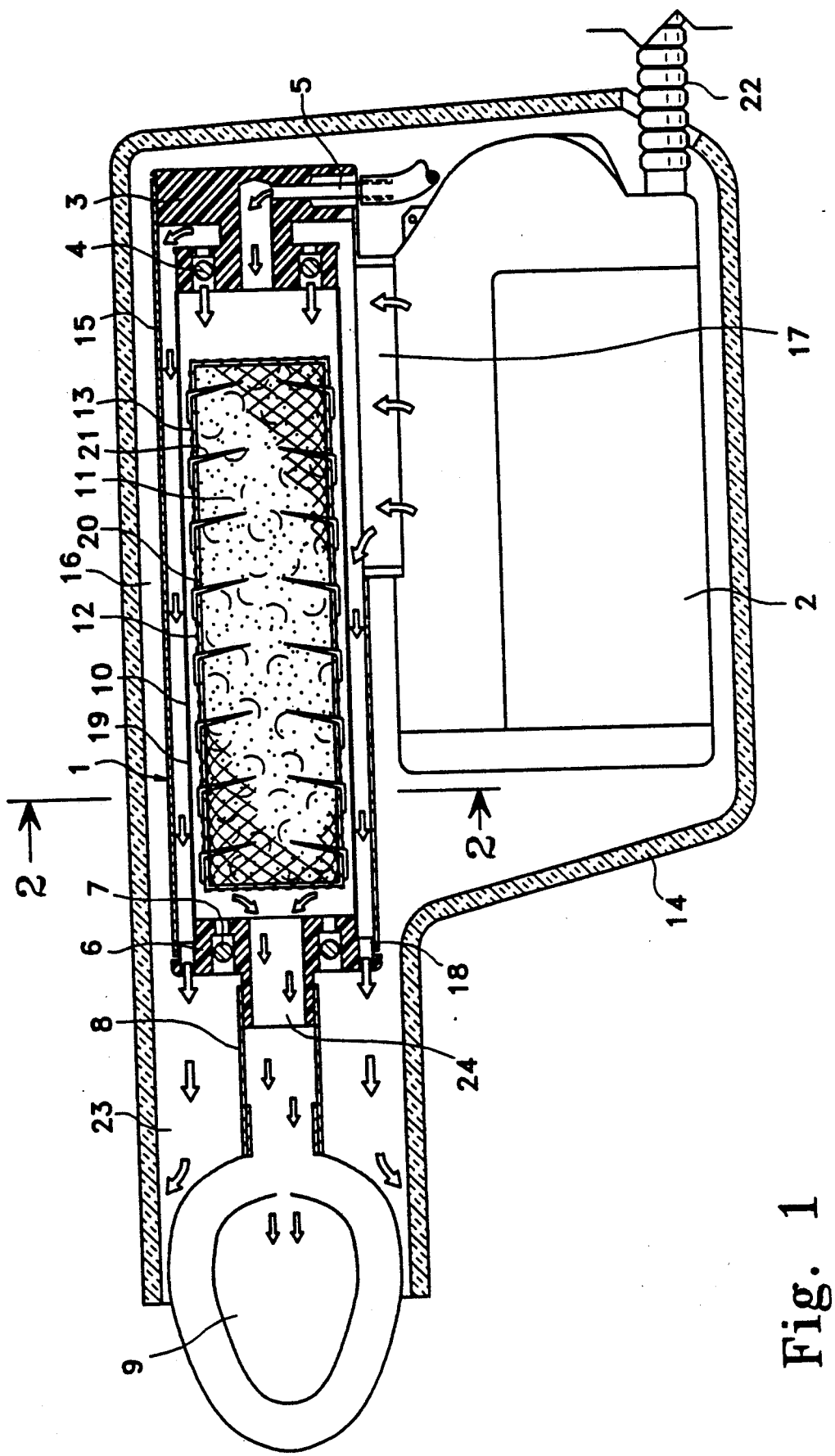
FIG. 1 shows an embodiment of the invention.

FIG. 1 shows portable means for adding heat and humidity to breathing air or oxygen. In a preferred embodiment it includes a charcoal fuel element heater 2 of the type described in U.S. Pat. No. 4,664,674. This type of heater has a battery (D-cell) driven fan and thermostats for controlling the flow of combustion air and for the air to be heated. The details of the heater are not shown. Exhaust gases from the carbon combustion process are preferably passed through a catalyzing device before being expelled through a pipe 22 as $CO_2$ gases.

The heater 2 is integrated with a moisturized element 1, so that heated air from the heater 2 is humidified by being passed through the element 1. The heater 2 and element 1 are arranged within a heat insulating cover 14. The cover is provided with a number of apertures (not shown) for allowing environmental air to reach the heater air inlets. When placed within the jacket of a patent (with the $CO_2$ exhaust to the environments) the apparatus provides substantially to the heating of the patient.

The moisturized element 1 contains a body 11 of water absorbent material, such as fibre wadding or foamed polymer which is enveloped by an open-masked net 12. The purpose of the net 12 is to maintain the configuration of the body 11 and to ensure that there are first airspaces allowing passage of air/oxygen. The body 11 of water absorbent material is contained within a heat conducting first housing 10, so as to leave a first airspace 13 between substantial parts of the outer surface of the body 11 and the inner surface of the first housing 10. The inner surface of the first housing 10 can be provided with elements (not shown) such as ribs and fins for improving the heat conduction from the housing to the air/oxygen within the first airspace 13. The first housing 10 can be of stainless steel. Oxygen may be supplied to the first airspace 13 either directly through an inlet 5 or alternatively partly via the heater 2. The body 11 of water absorbent material is provided with a heat insulation sheath 19 with apertures 20 through which there may be arranged a number of wicks 21 leading from the water absorbent material 11 to said first airspace 13. The sheath 19 may be of foamed polymer such as polyurethane. It is important that evaporation of water from the water absorbent body only takes place through the apertures 20, so that the operating temperature is reached quickly. The net 12 may be omitted if sufficient spacing to the first housing 10 is obtained by means of the wicks 21. The wick can be constituted by a fibre material such as cotton or polyprolylene.

The first airspace 13 is arranged between a first one-way valve means 4 leading from an air inlet 17 and an outlet pipe 24 leading to the breathing mask 9. The first one-way valve 4 is arranged to allow warm air from the heater 2 to enter the first housing 10 containing the body 11, and to close against air breathed out from the breathing mask 9. The second one-way valve 7 is arranged to allow air breathed-out from the breathing mask 9 to be exhausted, and to prevent environmental dry air from entering the first housing 10 through this valve during breathing in.

The inner first housing 10 is arranged within an outer second housing 15 of heat insulating material, defining the airspace 16 between the two housings. The second housing 15 has an inlet 17 leading from the outlet of the heater 2 to the second airspace 16 between the two housings 10 and 15 in order to heat the first housing 10. An outlet 18 from the second housing 15 being arranged close to the outlet valve 7 from the first housing 10. The body of water absorbent material 11, possibly with its first housing 10, is made like an exchangable unit fitted into the second housing 15 with an endpiece 6 defining an outlet from the second airspace 16. The breathing mask 9 is attached to the endpiece 6 with a flexible hose 8 which may be extendable. The endpiece contains the outlet valve 7 from the first housing 10.

In use, the apparatus works as follows. Warm air from the heater 2 flows through the air inlet 17 into the second airspace 16 between the two housings 10 and 15. The warm air heats the first housing 10 to a certain temperature and flows through the outlet 18 to an outlet compartment 23 close to the breathing mask 9. This provides comfortable heating of the face of the patient while breathing the humidified warm air/oxygen generated in the first airspace 13. A controlled amount of oxygen flows from the inlet 5, into the heated first housing 10, where the oxygen picks up heat and moisture from the wicks 21 in the first airspace 13.

When breathing in, oxygen will flow from the inlet 5 through the first airspace 13 inside the first housing 10 and pick up some moisture from the wicks 21. The oxygen will further flow through an outlet pipe 24 of the endpiece 6, into the mask 9 via the hose 8. The oxygen consumption is normally 8-10 liters per minute, with 0.7-0.9 grams of absorbed water vapor for the same period.

If the patient needs more than the provided amount of oxygen, he will automatically get what he needs of warm air through the valve 4. This air is moisturized as mentioned by the wicks 21 in the first airspace 13 and breathed into the mask 9. Environmental air is prevented from entering the system through the one-way valve 7. Due to the thermostat control of the heater 2, the temperature of the breathing oxygen will be substantially independent of the environmental temperature.

When breathing out, the used air is blown by the patient from the mask 9 through the pipe 24 and the outlet compartment 23 through the valve 7. The valve 4 is closed to this air flow direction. However, oxygen continues to flow into the first airspace 13 which acts as a buffer for comfortably heated and moisturized oxygen, waiting for the next breathing in. Very little oxygen is therefore lost.

The portable means has been described above in connection with the charcoal fuel element heater of U.S. Pat. No. 4,664,674. Other heater arrangements such as gas burners and fluid fuel based heaters can, however, also be used to heat the air and/or oxygen.

Figure 2:
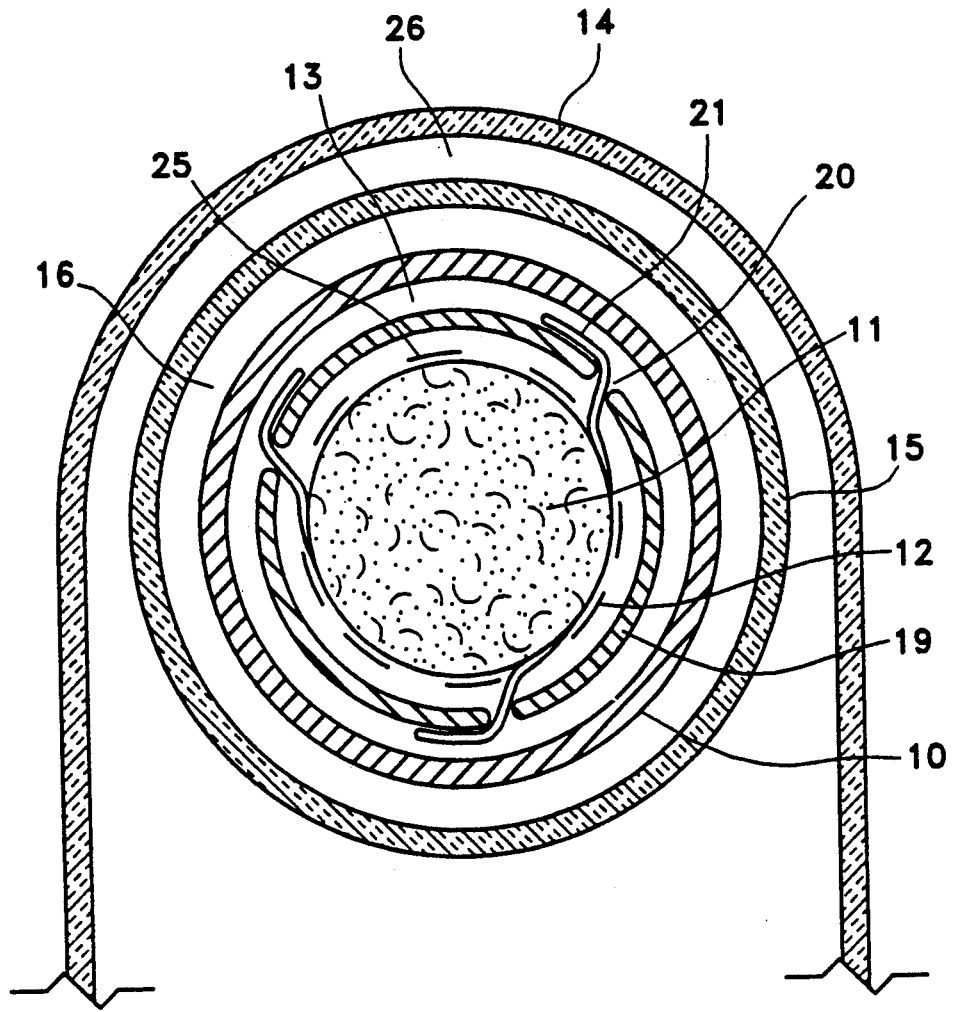
FIG. 2 shows a crossection of FIG. 1.

In FIG. 2 is schematically illustrated a crossection of humidifying device of FIG. 1 taken along the line II—II. The drawing shows the concentrical design of the device, starting with the body 11 of water absorbent material which may be enclosed within a net 12. The heat insulating sheath 19 is provided with apertures 20 through which wicks 21 may extend from the space 25 near the wet surface of the material 11, to the first airspace 13. The first airspace 13 which is defined by the heat conducting first housing 10 is used for transportation of warm humidified air/oxygen to the breathing mask 9, FIG. 1. The second airspace 16 which is defined by the heat insulating second housing 15 is used for transporting warm dry air to the face of the patient using the breathing mask. The second airspace 26 between the second housing 15 and the cover 14 is merely a buffer space for preventing loss of heat.

Figure 3:
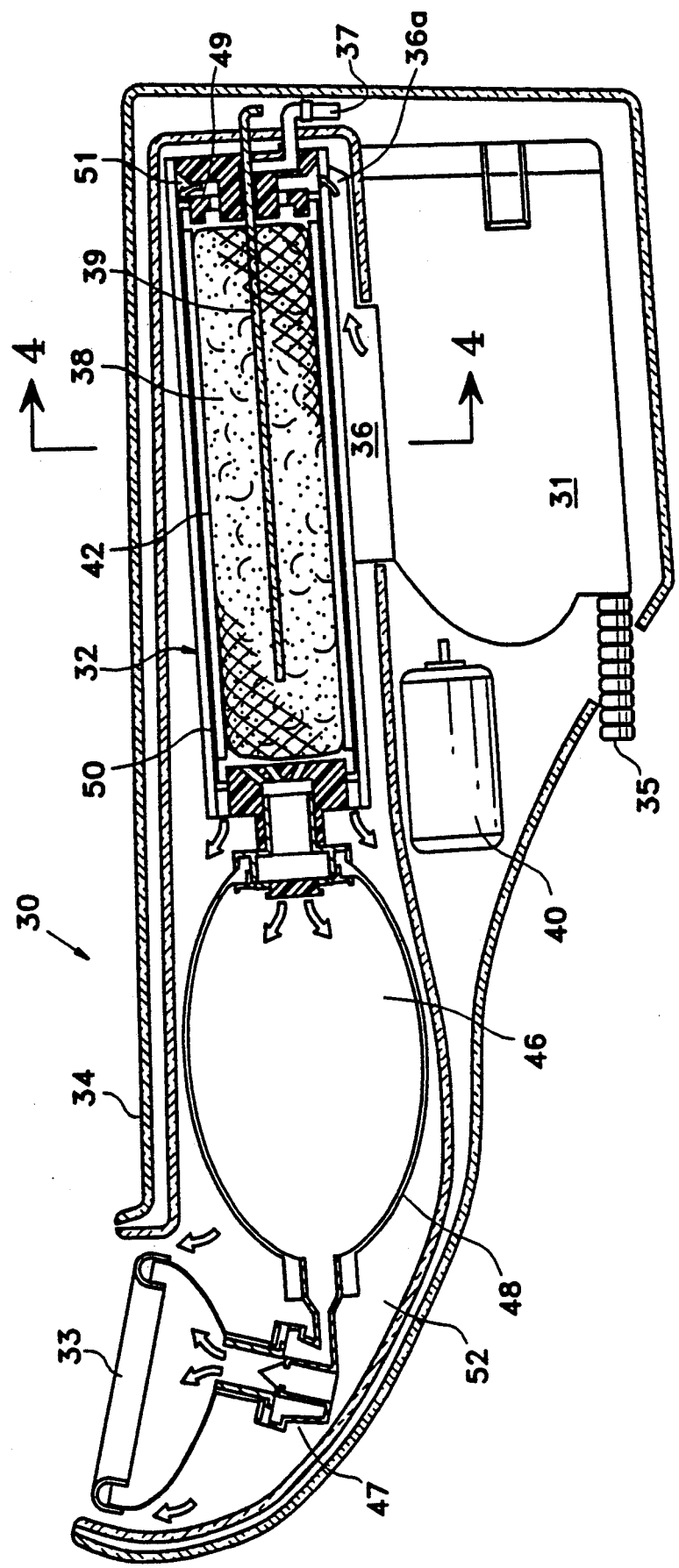
FIG. 3 shows an alternative embodiment.

In FIG. 3 is illustrated an alternative embodiment of the invention. The portable means 30 for adding heat and humidity to breathing air and/or oxygen includes a heater 31, a moisturized element 32 and a breathing mask 33. These elements are included within a flexible housing 34 of thermal insulating material, such as textile. The air inlets to the charcoal heater 31 are through the walls of the housing 34, the exhaust is indicated by a pipe 35 and its outlet—which is the air inlet to the element 32—is indicated at 36 and 36a. An oxygen supply is indicated at 37. Water supply means are inserted into the water absorbent body 38, consisting of a perforated plastic tubing 39 and a flexible water flask 40. The connection between the flask 40 and the tubing 39 is not shown. The water bottle 40 stores a sufficient amount of water for soaking the water absorping element 38. By pressing the bottle the water will be squeezed into the element 38.

Figure 4:
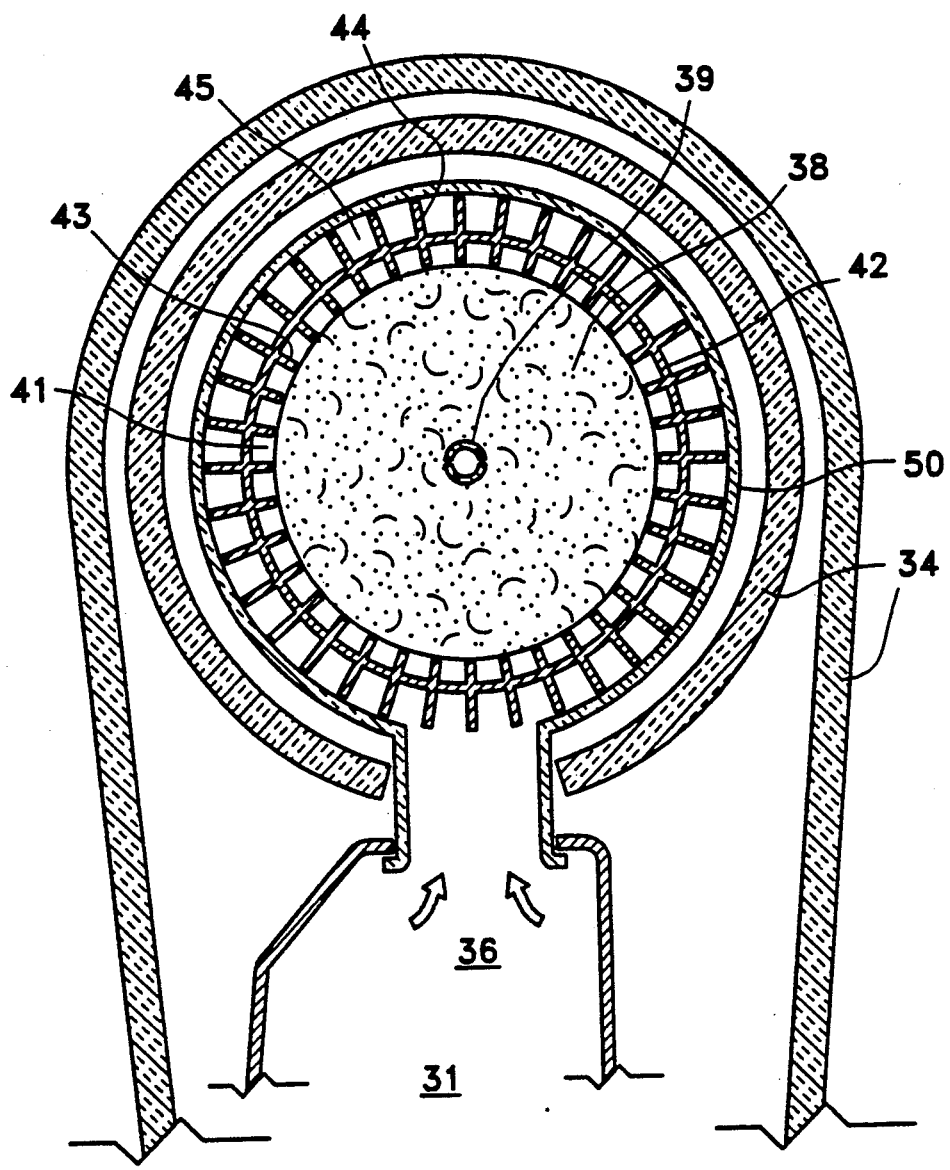
FIG. 4 shows a crossection of FIG. 3.

The first airspace 41, FIG. 4 over the body 38 for passing humid warm air and/or oxygen to the breathing mask 33 is defined by the inner walls of a heat exchanging device 42 consisting of a metal pipe with internal ribs or fins 43. The pipe may be made of aluminum. The pipe 42 is provided with ribs or fins 44 on its outside, thereby defining the second airspace 45 for passing dry warm air to the face of the patient.

The breathing oxygen/air flows in the first airspace 41 between the water absorbing element 38 and the inner finned surface of the heat exchanger 42 here picking up heat and oxygen/air. The air is supplied through inlet 36, the oxygen through the inlet 37. The warm wetted air/oxygen is passed from an outlet 46 through a conventional valve arrangement 47 to the breathing mask 33. This valve 47 has an outlet (not shown) for used air. A ventilation bag 48 may be arranged in the air/oxygen path between the outlet 46 of the device in front of the breathing mask 33. The purpose of the ventilation bag 48 is to enable 'pumping' of air/oxygen into the breathing mask for resuscitation of a patient. The one way valve arrangements 47 and 49 will prevent the air/oxygen to be pushed (pumped) out (to the right in the drawing) of the tube 42.

While the warm humidified oxygen/air flows through the ventilation bag and into the mask, it should be noted that warm air will automatically substitute for oxygen in the case of insufficient oxygen supply. There will then automatically be a flow of warm air through the breathing warm air valves. The oxygen inlet 37 may also be connected to an external oxygen reservoir bag (not shown) thereby ensuring efficient and economic use of oxygen.

The second airspace 45 on the outside of the heated metal tube is defined by an outer shell 50 with low heat conductivity. Warm air from the heater 31 flows into a front chamber 51, then along the outer fins 44 of the heat exchanger 42 into the space 52 surrounding the ventilation bag 48. Further, the warm air passes the upper surface of the mask 33 before being discharged over the face of the patient.

In FIG. 4 is shown a crossection of FIG. 3 taken along the line IV—IV and all elements are described in connection with FIG. 3.

We claim:

1. Portable device for adding heat and humidity to a breathing gas, said device comprising
a breathing mask,
a moisturized element in the form of a coaxial arrangement of
a body of water absorbent material,
a heat conducting first housing having an outlet and
a first coaxial airspace between said body and said first housing for transportation of humidified warm air to the breathing mask,
a temperature controlled and fan operated charcoal fuel element heater integrated with the moisturized element so that heated air from the heater is humidified by passing it through the moisturized element, and
water supply means for soaking the water absorbent body with water.

2. Device according to claim 1, wherein the water supply means comprises a perforated plastic tubing inside the water absorbent body connected to a flexible flask for storing a supply of water.

3. Device according to claim 1, further comprising an oxygen supply connected to the first airspace.

4. Device according to claim 3, wherein the oxygen supply is connected to the first airspace via the heater.

5. Device according to claim 3 wherein said breathing gas is environmental air enriched with oxygen from said oxygen supply.

6. Device according to claim 1, wherein a ventilation bag is arranged between the breathing mask and the outlet of the first housing.

7. Device according to claim 1, wherein the heater and the moisturized element are included within a cover made of heat insulating material and having apertures for air inlet to the heater.

8. Device according to claim 1, wherein said body of water absorbent material is fibre wadding.

9. Device according to claim 1, wherein said body of water absorbent material is foamed polymer.

10. Device according to claim 1 wherein said breathing gas is environmental air.

11. Portable device for adding heat and humidity to breathing air, said device comprising
a breathing mask,
a moisturized element in the form of a coaxial arrangement of
a body of water absorbent material,
a heat insulation sheath surrounding said body,
a housing
a coaxial airspace between said sheath and said housing for transportation of the breathing gas to the breathing mask, and
a plurality of wicks extending through respective apertures in said heat insulation sheath and leading from the water absorbent material to said coaxial airspace, and
a heater integrated with the housing so that breathing air is heated and humidified by passing through said coaxial airspace before it is transported to the breathing mask.

12. Portable device for adding heat and humidity to breathing air, said device comprising
a breathing mask,
a moisturized element in the form of a coaxial arrangement of
a body of water absorbent material,
a first housing and
a first coaxial airspace between said body and said first housing for transportation of the breathing air from an inlet to an outlet,
means for coupling the outlet of the coaxial airspace to the breathing mask,
a heater integrated with the housing such that breathing air is heated and humidified as it passes through the coaxial airspace, and
a first one-way valve between the heater and the first coaxial airspace, arranged such that breathing air may flow from the heater to the breathing mask via the first coaxial passage but not from the first coaxial airspace to the heater.

13. Device according to claim 12, wherein the first housing is arranged within a heat insulating second housing having an inner wall which cooperates with an outer wall of the first housing to define a second coaxial airspace through which dry warm air from the heater is transported to the face of a person breathing the humidified air.

14. Device according to claim 13, wherein the water absorbent material is in the form of an exchangeable unit fitted into the second housing with an endpiece defining an outlet from the second airspace.

15. Device according to claim 12, wherein
the breathing mask is attached to the endpiece with a hose, and
the endpiece contains an outlet valve from the first housing.

16. Device according to claim 12 wherein the first housing is part of the exchangeable unit fitted into the outer housing.

17. Portable device for adding heat and humidity to a breathing gas, said device comprising
a breathing mask,
a moisturized element in the form of a coaxial arrangement of
a body of water absorbent material,
a heat conducting first housing and
a first coaxial airspace between said body and said first housing for transportation of the breathing gas from a first inlet to a first outlet, means for coupling the first outlet to the breathing mask, means for coupling the first inlet to a source of said breathing gas, a heater having an outlet for providing a source of heated air, and a heat insulating second housing surrounding an outer wall of the heat conducting first housing and having an inner wall which cooperates with said outer wall to define a second coaxial airspace, said second coaxial airspace having a second inlet directly coupled to the outlet of the heater for admitting heated air from the heater and a second outlet adjacent to said first outlet for expelling warm, dry air in the direction of the face of a person breathing the humidified air from the first outlet after the warm, dry air has passed through the second coaxial airspace and thereby heated the breathing gas in the first coaxial airspace via the heat conducting first housing.

18. Portable device for adding heat and humidity to a breathing gas, said device comprising a breathing mask, a moisturized element in the form of a coaxial arrangement of a body of water absorbent material, a heat exchanging device surrounding said body of water absorbent material, said heat exchanging device further comprising a metal pipe with internal fins or ribs, a first coaxial airspace defined by the inner walls of said heat exchanging device, for transportation of humidified warm air to the breathing mask, and a heater integrated with the heat exchanging device so that the breathing gas is heated and humidified by passing through said coaxial airspace before it is transported to the breathing mask.

19. Device according to claim 18, wherein the heat exchanging device is provided with outer ribs or fins extending outwardly to an inner wall of a second housing to thereby define passages for warm dry air through a second coaxial airspace.

20. The device of any of claims 11, 12, 17, 18, or 19, wherein the heater is a temperature controlled and fan operated charcoal fuel element heater.

21. Portable device for adding heat and humidity to a breathing gas, said device comprising a breathing mask, a moisturized element in the form of a coaxial arrangement of a body of water absorbent material, a heat conducting first housing and a first coaxial airspace between said body and said first housing for transportation of humidified warm air to the breathing mask, a temperature controlled and fan operated charcoal fuel element heater integrated with the moisturized element so that heated air from the heater is humidified by passing it through the moisturized element, and an oxygen supply directly connected to the first airspace.

22. Portable device for adding heat and humidity to oxygen-enriched breathing air, said device comprising a breathing mask, a source of oxygen enriched air, a moisturized element in the form of a coaxial arrangement of a body of water absorbent material, a heat exchanging device surrounding said body of water absorbent material, a first coaxial airspace defined by said body of water absorbent material and an inner wall of said heat exchanging device, said first coaxial airspace having a first inlet in communication with said source and a first outlet in communication with the breathing mask, means for coupling said first outlet to the breathing mask, a heater integrated with the heat exchanging device such that the oxygen enriched air is heated and humidified as it passes through the coaxial airspace, a one-way valve between the heater and the first coaxial passage, arranged such that heated air may flow from the heater into the first coaxial passage but not from the first coaxial passage to the heater, and a heat insulating housing surrounding an outer wall of the heat exchanging device and having an inner wall which cooperates with said outer wall to define a second coaxial airspace, said second coaxial airspace having an inlet directly coupled to the outlet of the heater for admitting heated air from the heater and a second outlet adjacent to said first outlet for expelling warm, dry air in the direction of the face of a person breathing the humidified air from the first outlet after it has passed through the second coaxial airspace and heated the oxygen enriched air in the first coaxial airspace.

23. The device of claim 22, wherein the heater is a temperature controlled and fan operated charcoal fuel element heater.

* * * * *